(12) United States Patent
Bellaton et al.

(10) Patent No.: US 10,436,688 B2
(45) Date of Patent: Oct. 8, 2019

(54) HEATING ARRANGEMENT FOR A MATERIAL TESTING DEVICE

(71) Applicant: ANTON PARR TRITEC SA, Peseux (CH)

(72) Inventors: Bertrand Bellaton, Neuchâtel (CH); Marcello Conte, Neuchâtel (CH)

(73) Assignee: ANTON PAAR TRITEC SA, Peseux (CH)

( * ) Notice: Subject to any disclaimer, the term of this patent is extended or adjusted under 35 U.S.C. 154(b) by 225 days.

(21) Appl. No.: 15/522,309

(22) PCT Filed: Nov. 2, 2015

(86) PCT No.: PCT/EP2015/075490
§ 371 (c)(1),
(2) Date: Apr. 27, 2017

(87) PCT Pub. No.: WO2016/071295
PCT Pub. Date: May 12, 2016

(65) Prior Publication Data
US 2017/0336308 A1   Nov. 23, 2017

(30) Foreign Application Priority Data

Nov. 3, 2014   (EP) .................................... 14191443

(51) Int. Cl.
| | |
|---|---|
| *G01N 3/04* | (2006.01) |
| *B01L 7/00* | (2006.01) |
| *G01N 3/42* | (2006.01) |
| *G01N 21/37* | (2006.01) |

(52) U.S. Cl.
CPC .................. *G01N 3/04* (2013.01); *B01L 7/52* (2013.01); *G01N 21/37* (2013.01); *G01N 3/42* (2013.01); *G01N 2203/0226* (2013.01)

(58) Field of Classification Search
CPC .... G01N 3/04; G01N 3/42; G01N 2203/0226; B01L 7/52
USPC .............................................. 73/81
See application file for complete search history.

(56) References Cited

U.S. PATENT DOCUMENTS

| | | | |
|---|---|---|---|
| 3,600,553 A | 8/1971 | Costello | |
| 3,763,348 A | 10/1973 | Costello | |
| 3,764,772 A * | 10/1973 | Matuschek | B23K 1/0053 |
| | | | 219/85.12 |
| 4,184,065 A | 1/1980 | Nagashima | |
| 4,695,705 A * | 9/1987 | Kulig | A61C 19/003 |
| | | | 392/418 |

(Continued)

*Primary Examiner* — Natalie Huls
*Assistant Examiner* — Monica S Young
(74) *Attorney, Agent, or Firm* — Duane Morris LLP; Gregory M. Lefkowitz; Jason M. Nolan (57) ABSTRACT

Heating arrangement for a materials testing device, the materials testing device comprising at least one surface measurement probe adapted to be brought into contact with a surface of a sample, the heating arrangement comprising a probe heater comprising:
an infrared emitting element adapted to emit infrared radiation;
a reflector having a reflective surface arranged to direct said infrared radiation towards a distal end of said surface measurement probe.
According to the invention, the reflector comprises a first focal point and a second focal point, the infrared emitting element being situated substantially at said first focal point.

17 Claims, 4 Drawing Sheets

(56) References Cited

U.S. PATENT DOCUMENTS

| | | | | |
|---|---|---|---|---|
| 5,762,707 A | * | 6/1998 | Shindo | C30B 13/24 |
| | | | | 117/200 |
| 5,777,330 A | * | 7/1998 | Murase | G01N 21/3563 |
| | | | | 250/339.13 |
| 5,805,769 A | | 9/1998 | Cook et al. | |
| 6,313,582 B1 | * | 11/2001 | Miyanaga | H01J 61/363 |
| | | | | 313/570 |
| 6,684,677 B1 | * | 2/2004 | Bar | B21D 1/06 |
| | | | | 72/342.1 |
| 2006/0016448 A1 | * | 1/2006 | Ho | F21S 11/00 |
| | | | | 126/698 |
| 2008/0135542 A1 | * | 6/2008 | Adames, Sr. | H05B 3/18 |
| | | | | 219/520 |
| 2009/0268283 A1 | * | 10/2009 | Borucki | G02B 21/34 |
| | | | | 359/391 |
| 2014/0165702 A1 | * | 6/2014 | Tanabe | G01N 29/022 |
| | | | | 73/24.06 |
| 2014/0326707 A1 | | 11/2014 | Schmitz | |

\* cited by examiner

HEATING ARRANGEMENT FOR A MATERIAL TESTING DEVICE

CROSS-REFERENCE TO RELATED APPLICATIONS

This application is a § 371 national stage entry of International Application No. PCT/EP2015/075490, filed Nov. 2, 2015, which claims priority to European Patent Application No. 14191443.2, filed Nov. 3, 2014, the entire contents of which is incorporated herein by reference.

TECHNICAL FIELD

The present invention relates to the field of surface testing of materials. More particularly, it relates to a heating arrangement for a materials testing device such as an indenter.

STATE OF THE ART

Materials science requires detailed knowledge of mechanical properties of materials, surfaces and coatings even on the nano-scale, and also the temperature dependence of these properties. Indentation testing allows determination of Young's modulus, hardness, strain rate sensitivity, tribological properties etc. on any scale. Measurements at micrometer and nanometer scales are particularly useful, and can permit measurements of the properties of single crystals in a multi-crystalline structure.

Many systems have been developed to perform such measurements at elevated temperatures, since many of these properties are temperature-dependent, particularly when a material exhibits a crystal phase change or a glass transition temperature. However, the probe tip must equally be heated to the same temperature as the sample to prevent localised cooling of the hot sample causing thermal expansion of the tip and thermal contraction of the sample, which affects the accuracy of the measurements. However, there is also the further constraint that the heating must be kept as localised as possible to the sample and to the tip so as to avoid heating the entire system, which would again affect the accuracy of the measurements by inducing thermal expansion in other components of the system. Furthermore, this can introduce thermal drift into the measurements.

Various strategies have been developed to deal with this issue.

For instance, WO 2013/074623 describes a heating assembly configured for use in mechanical testing at a scale of microns or less. The probe tip assembly includes a probe tip heater system having a heating element embedded in the probe.

US 2010/0212411 describes a tip indenting apparatus comprising a solid body made of heat conducting material heated up by an electrical member helically wound around the outer wall, so as to heat the probe tip.

Such systems incorporating heating elements integrated into the probe tip are however not satisfactory: they are bulky and thus result in heating of a relatively large amount of material, which is undesirable both in terms of thermal expansion and also in terms of thermal inertia. Significant thermal inertia results in time lags and thus control instability when manipulating the temperature of the tip. Furthermore, the temperatures which can be achieved are somewhat limited, as are the temperatures at which measurement repeatability is good.

An alternative solution has been proposed by SURFACE systems+technology GmbH & Co KG, which involves laser heating of an indentation tip. However, the maximum temperature attainable at the tip is approximately 500° C., which is inadequate for many applications. Other known arrangements include heating the probe by induction, however this generates significant electromagnetic interference which can affect the operation of sensitive measurement devices.

In respect of heating arrangements more generally, U.S. Pat. No. 5,777,330 describes a heater for pyrolising plastic so as to identify its composition by infrared spectroscopy.

U.S. Pat. No. 4,184,065 describes a heating apparatus with an ellipsoidal reflecting mirror for heating a rod which passes through part of the mirror, and is melted by concentrated infrared radiation. This arrangement is used in a system for crystallization of refractory oxides.

U.S. Pat. No. 3,600,553 describes a heating apparatus with multiple focal points, on one of which is situated a source of infrared radiation. The reflector is formed in two halves which are hinged at their apex and, by adjusting the relative position of the two halves, one or two focal points can be created, and in the case of two focal points, the separation of these points can be that, for instance, two leads extending from opposite sides of an integrated circuit body can be simultaneously soldered to the associated conductive coatings in a single soldering operation without overheating the integrated circuit itself.

U.S. Pat. No. 5,805,769 describes a food heating apparatus which incorporates a plurality of ellipsoidal reflectors so as to create a charbroiled surface effect on the food.

U.S. Pat. No. 3,763,348 describes an apparatus for irradiating a surface in a uniform manner, which uses an ellipsoidal reflector for substrate heating and photocopying.

U.S. Pat. No. 5,762,707 describes a floating zone melting apparatus for growing large single crystals. This apparatus uses a plurality of ellipsoidal reflectors to concentrate infrared radiation on a rod of material.

However, none of these heating arrangements are suitable for use in a materials testing device for reasons of structural incompatibility or optical reasons. Indeed, several of the arrangements mentioned in these documents relate to providing a uniform radiation over a surface or radiation concentrated on several discrete spots, which are the opposite of the single, concentrated focal point required to heat an indentation probe tip. Furthermore, none of the documents mentioned suggest either implicitly or explicitly the use of such arrangements for overcoming any of the drawbacks of existing heating arrangements for materials testing devices as discussed above.

An object of the invention is thus to overcome at least some of these drawbacks of the prior art, and thus to propose a heating system for a materials testing device which is usable over a wide temperature range and has a low thermal inertia.

DISCLOSURE OF THE INVENTION

This aim is attained by a heating arrangement for a materials testing device, the materials testing device comprising at least one surface measurement probe adapted to be brought into contact with a surface of a sample. The heating arrangement comprising a probe heater comprising an infrared emitting element adapted to emit infrared radiation, and a reflector having a reflective surface arranged to direct said infrared radiation towards a distal end of said surface measurement probe.

According to the invention, the reflector comprises a first focal point and a second focal point, the infrared emitting element being situated substantially at said first focal point.

As a result, a concentrated beam of infrared radiation can be created from any convenient infrared emitting element, such as but not limited to a halogen lamp, a ceramic heater, a laser or similar, which can then be focused as desired upon the probe. With such an arrangement it is possible to achieve higher temperatures than with a laser, and the infrared radiation can be focused more or less sharply upon the probe as required so as to avoid localised hotspots.

Advantageously, the reflector is formed and positioned such that said second focal point is situated substantially at a part of the surface measurement probe, such as at or near its distal end.

Advantageously, said reflector is substantially ellipsoidal on at least part of its reflective surface. Such a shape exhibits the desired two focal points, and is easy to machine with conventional tooling.

Advantageously, the reflector further comprises a mask section at an open end thereof. This mask, which may for instance be conical (i.e. formed as a tapered nose) or may be an annular mask, prevents extraneous, unfocused infrared radiation from leaving the reflector and heating undesired parts of the system.

Advantageously, infrared emitting element is an incandescent lamp such as a halogen lamp. Such lamps are cheap, off-the-shelf components which are easily replaced, and have very low thermal lag since the filament has a low mass and a correspondingly low heat capacity. As a result of this latter property, excellent responsiveness and control stability can be achieved with low time lag. Alternatively, the infrared emitting element can be a ceramic heater.

Advantageously, said reflector comprises an infrared-reflective coating such as a gold, silver, platinum, rhodium, ruthenium, aluminium or platinum coating. Such a coating serves to limit the absorption of infrared radiation by the reflector, and thus to maximise the maximum temperature of the probe which is attainable.

Advantageously, the heating arrangement further comprises a sample heating module. Although any form of sample heating module can be used in the heating arrangement, this particularly advantageous sample heating module is adapted to support a sample such that it can be contacted by the probe, and comprises at least one further infrared emitting element adapted to emit infrared radiation and a further reflector having a further reflecting surface adapted to direct said infrared radiation emitted by the further infrared emitting element towards the sample. The sample can thus be supported and heated to the desired temperature.

Advantageously, the further reflector is substantially parabolic, which results in even heating of the sample without hotspots.

Advantageously, the further reflector is comprised in a block provided with a cooling arrangement. This minimises re-radiation of infrared from the further reflector.

Advantageously, said further reflecting surface is formed directly on said block, which ensures excellent thermal coupling and minimises the number of components. The reflector may also comprise an infrared-reflective coating such as a gold, silver, platinum, rhodium, ruthenium, aluminium or platinum coating.

Advantageously, the heating arrangement comprises a sample holder adapted to support said sample, the sample holder being mounted in an insulating ring and situated facing an open face of said further reflector. The sample holder may be of alumina. An annular cap may be provided covering the insulating ring and a peripheral part of said sample holder. This annular cap prevents extraneous infrared radiation from propagating in undesired directions, or being absorbed by undesired objects. Advantageously, the annular cap is provided with an infrared-reflective coating such as a gold, silver, platinum, rhodium, ruthenium, aluminium or platinum coating on at least one surface thereof to minimise absorption of infrared radiation by the cap.

The aim of the invention is likewise attained by a materials testing device comprising at least one surface measurement probe adapted to be brought into contact with a surface of a sample and a heating arrangement as described above.

This materials testing device may comprise a headstock adapted to support said surface measurement probe and a heatsink attached to said headstock, the heatsink defining an interior cavity surrounding said surface measurement probe, the probe heater being mounted in a passage provided in the heatsink which opens into said interior cavity. This interior cavity may optionally provided with an infrared-reflective coating such as a gold, silver, platinum, rhodium, ruthenium, aluminium or platinum coating.

In consequence, transmission of heat to the headstock can be minimised as far as possible.

Advantageously, the reflector of the probe heater is formed integrally with the heatsink, improving heat flow by eliminating the material junction between the reflector and the heatsink.

BRIEF DESCRIPTION OF THE DRAWINGS

Further details of the invention will appear more clearly in the following description in reference to the figures, which show.

EMBODIMENT OF THE INVENTION

Figure 1:
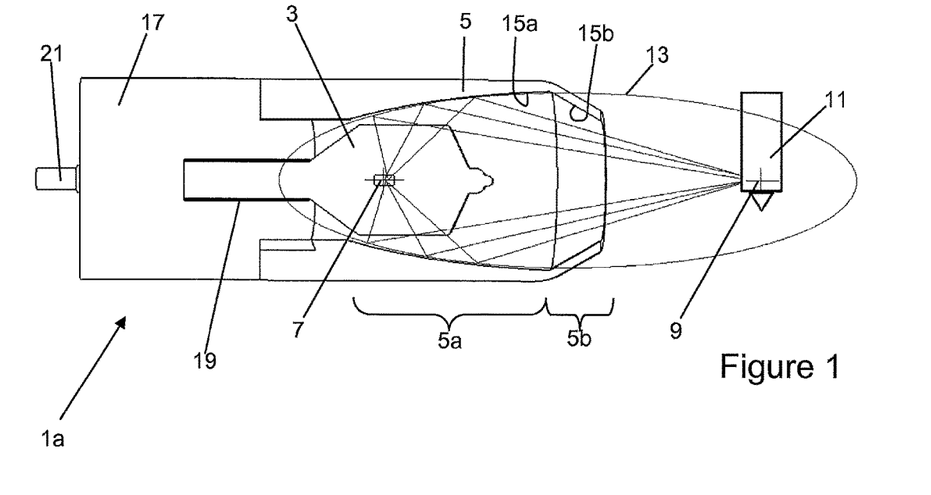
FIG. 1: a schematic view of a probe heater.

FIG. 1 illustrates schematically the basic principle of a probe heater 1a comprised in a heating arrangement according to the invention.

The heating arrangement comprises a probe heater 1a comprising an infrared emitting element 3 such as an incandescent lamp (e.g. a halogen lamp), a ceramic heating element, a laser, or similar. Halogen lamps are particularly advantageous because they are cheap, easily replaced, available off-the-shelf, and the filament can easily attain temperatures in the region of 3000 K at relatively low currents. Such an infrared emitting element 3 is illustrated in the present embodiment. Typical power would be around 150 W, however powers as low as 35 W are adequate for certain applications Furthermore, such lamps emit energy in both the visible and infrared wavelength ranges, with a broad spectrum, and have a low thermal inertia due to their low mass, and thus the low heat capacity, of the filament. Their temperature can thus be very easily and very quickly regulated by varying the current passing therethrough, with a relatively rapid response time.

Infrared emitting element 3 is situated in the concave interior of a reflector 5. Reflector 5 is formed having a reflective surface 15a shaped so as to exhibit a first focal point 7, at which the hot part of infrared emitting element 3, e.g. the filament of a halogen lamp, is situated, and a second focal point 9, at which the tip of a surface measurement probe 11 is situated. It should be borne in mind that focal points 7, 9 do not have to be absolutely perfect infinitesimal points, but may be somewhat diffuse, and the exact position of the infrared emitting element 3 in the reflector 5 can be adjusted to optimise the shape of the infrared beam. It may for instance be advantageous to arrange the focal points to cover a volume substantially corresponding to that of the object situated therein, such that a maximum of the energy emitted by the infrared emitting element 3 is captured, and subsequently transferred to the relevant part of the surface measurement probe 11, which is then heated as evenly as possible. Experiments have shown that temperatures up to 800° C. or even up to 1000° C. are easily attainable for the surface measurement probe 11 with the heating arrangement of the invention.

An example of a reflector shape which exhibits the required two focal points is an ellipsoidal reflector, which comprises a concave reflecting surface 15a substantially following the shape of an ellipse 13, in a primary reflecting section 5a of the reflector 5. Slight deviation from a mathematically perfect ellipse is likely in view of manufacturing tolerances, and may indeed be desirable in the case that it is desired that the focal points should be diffuse. Indeed, this deviation can be precisely calculated so as to determine the size and shape of the focal points as desired.

Concave reflecting surface 15a is ideally coated with a highly infrared reflective material such as gold, silver, platinum, rhodium, ruthenium, aluminium or platinum so as to provide a highly-reflective finish, and to minimise absorption of infrared by the material of the reflector 5. Any convenient material may be used for reflector 5, such as aluminium, steel, or a ceramic, a glass, or a glass-ceramic. In the case of a metallic material being chosen for reflector 5, such a coating is not strictly necessary can be dispensed with since the material of the reflector 5 can be simply polished to a high finish. It should be noted that reflector 5 may also be provided with cooling means such as conduits for water or any other convenient coolant, so as to prevent lateral emission of infrared radiation from the body of the reflector 5 if it heats up.

In order to prevent extraneous infrared radiation from impinging on other components of the materials testing device in which the probe heater 1a is integrated, reflector 5 furthermore comprises a mask section 5b. In the illustrated example, mask section 5b comprises a masking surface 15b of conical form, which serves to block infrared radiation which is not travelling on a path towards the second focal point 9. Such radiation may emanate from scattering effects on the concave reflecting surface 15a, or from refractions caused by the encapsulating material of the infrared emitting element 3 (e.g. the outer glass of a halogen lamp). To this end, masking surface 15b may be finished so as to absorb infrared radiation and may thus be rough, matt, black-coloured or similar. For instance, in the case of an aluminium reflector 5, masking surface 15b may be black anodised, while reflecting surface 15a is polished to a high finish and/or coated in e.g. gold, silver, platinum, rhodium, ruthenium, aluminium or platinum.

Other shapes of mask section 5b are also possible, such as a simple annular mask attached to the end of primary reflecting section 5a.

Reflector 5 is attached to a terminal element 17, e.g. of ceramic, which comprises a socket 19 to support infrared emitting element 3 and to provide electrical connection thereto, and electrical contacts 21 for supplying power to the infrared emitting element 3. Alternatively, terminal element 17 can be an integral part of the infrared emitting element 3 which is exchanged in its entirety if the infrared emitting element 3 needs replacing.

Figure 2:
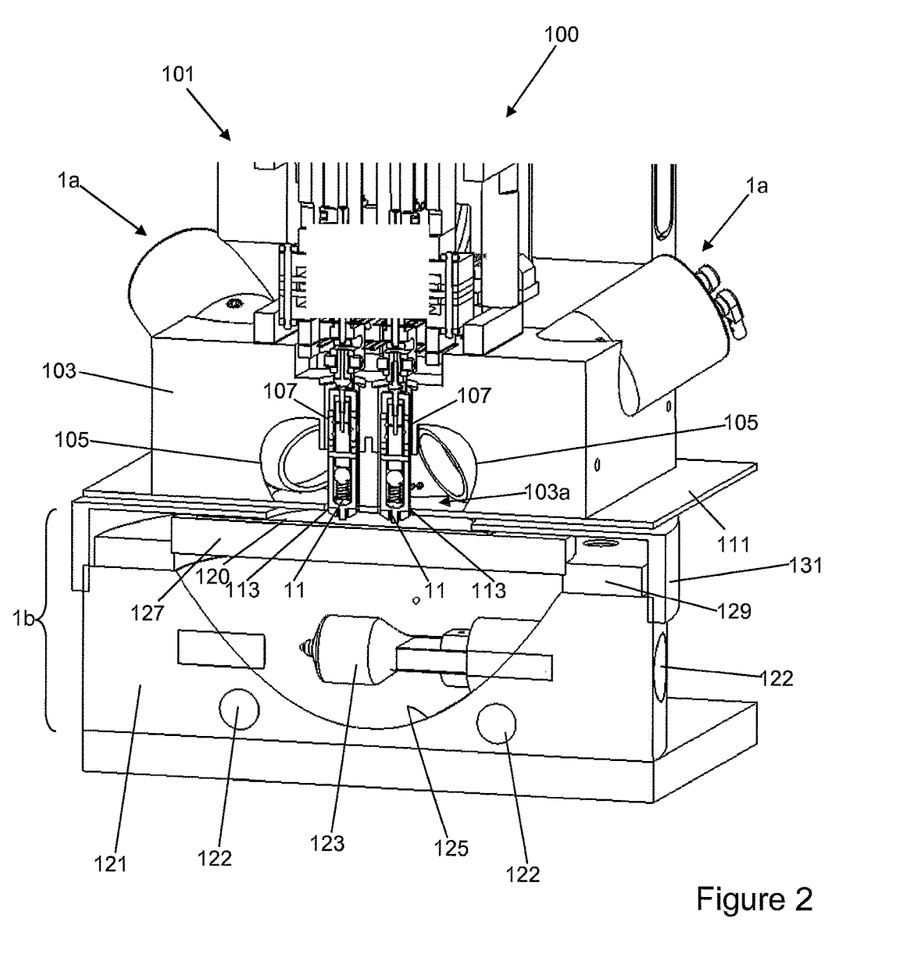
FIG. 2: a perspective cutaway view of a materials testing device incorporating the heating arrangement of the invention.
Figure 3:
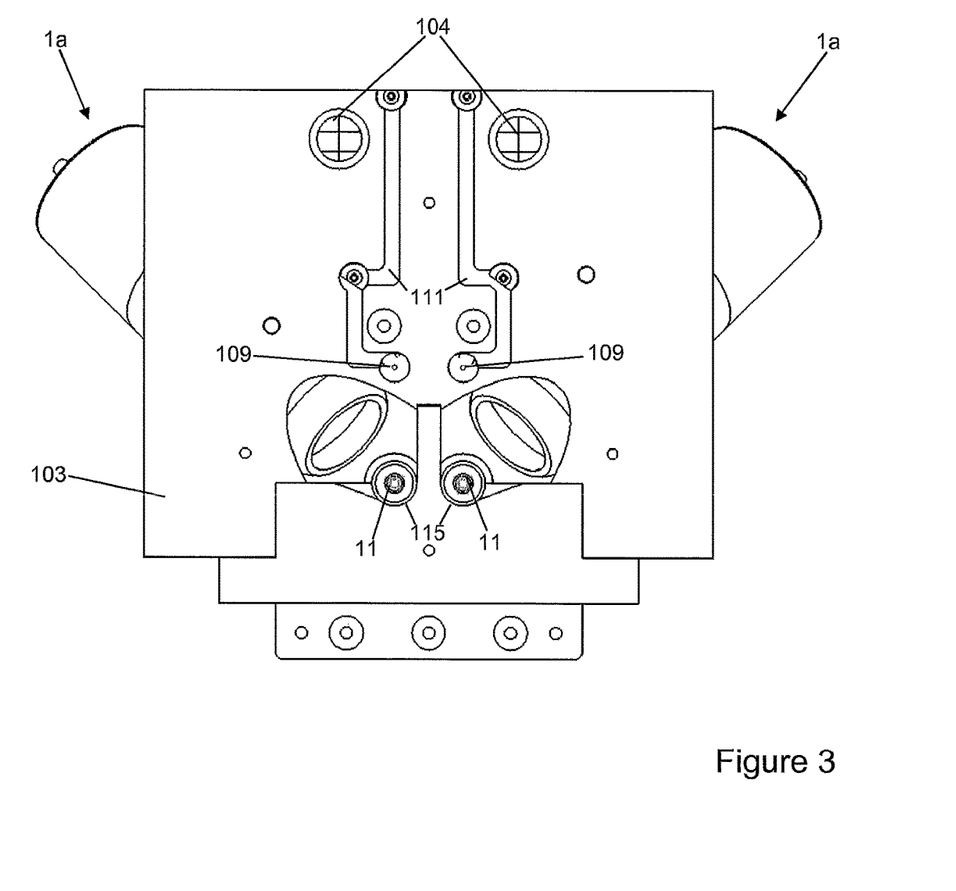
FIG. 3: an underside view of part of the materials testing device of FIG. 2.

FIG. 2 illustrates a perspective cutaway view of a materials testing device 100, in which a pair of probe heaters 1a, and a sample heating module 1b have been integrated. Sample heating module 1b will be described in greater detail below. FIG. 3 illustrates a view from underneath the materials testing device 100, viewed from the position of the sample, base plate 111 having been removed. As illustrated, the materials testing device 100 is a nanoindenter adapted to operate on a nanometer scale, but could equally be a micro indenter or a conventional indenter such as a Vickers indenter.

Materials testing device 100 comprises a headstock 101 of any convenient type, such as those marketed by the present applicant, which serves as a support for a pair of surface measurement probes 11 such as those described in the co-pending application filed the same day by the present applicant. Such a headstock typically comprises means for applying forces to the probes 11, and means for measuring the forces applied to, and/or the displacement of, the probes 11. It should be noted that any other convenient surface measurement probes may be used, and that the present invention is not limited to use with a particular type of surface measurement probe. As is generally known, one of said pair of surface measurement probes 11 would typically be arranged as a reference probe, the other as an indentation probe, and these probes 11 are positioned so as to be brought into contact with the surface of a sample 120 in the conventional fashion.

As can be seen in FIG. 2, materials testing device 100 further comprises a heatsink 103 attached to the headstock 101, through which are provided passages 105 shaped so as to receive probe heaters 1a such that the probe heaters 1a are mounted therein and are intimately thermally coupled with the heatsink 103. The probe heaters 1a emerge in an internal cavity 103a in the heat sink and are arranged so as to focus infrared radiation on the probes 11 towards the distal ends thereof, and as such they are mounted at angle suitable to do so. It should be noted that it is also possible to form the reflector 5 and/or the mask section 5b of the probe heater 1a integrally with the heatsink 103. In such a case, terminal element 17 would interface directly with the heatsink 103. Such an arrangement assures the best possible removal of heat from the reflector 5, since there are no material junctions which might present a resistance to heat flow into the heatsink 103.

It should be noted that a further pair of probe heaters 1a may also be mounted at the reverse angle to those illustrated in FIG. 2, such that each probe 11 is heated by a pair of probe heaters 1a.

In the case in which the temperature of the probes 11 and the sample 120 must be maintained for more than a few seconds, heatsink 103 may be watercooled by water flowing in conduits 104 (see FIG. 3) provided in the heatsink 103. Various internal surfaces of the heatsink 103 may be provided with a reflective coating such as a gold, silver, platinum, rhodium, ruthenium, aluminium or platinum coating so as to minimise absorption of infrared radiation areas in which this is undesired, such as surrounding the openings of the reflector is 5, and the areas surrounding the probes 11. As a result, an infrared bath is provided in which the tips of the probes 11 are bathed. Essentially, the aim is to retain as much infrared radiation in the area of the probes as possible by reflection, while keeping the surrounding material cool and thereby preventing re-emission of absorbed infrared radiation.

The probes 11 pass through corresponding bores 107, to minimise heat reaching the headstock 101, the probes 11 and the bores 107 are threaded in an area towards the proximal end of the probes 11, and are screwed together. This increases thermal contact between the probes 11 and the heatsink 103, maximising heat transfer into the heatsink 103 and keeping the headstock 101 as cool as possible. This heat transfer can be maximised by e.g. painting or otherwise coating the threads with an absorbent material such as black paint, black anodised aluminium or similar. The lower end of the bores 107 (i.e. the end towards the sample 120) is not threaded and may be coated with infrared reflective material such as gold, silver, platinum, rhodium, ruthenium, aluminium or platinum.

So as to contain as much of the infrared radiation around the distal ends of the probes 11 as possible and thereby to minimise heating the sample 120 by means of the probe heaters 1a, a base plate 111 is attached to the underside of the heatsink 103. This base plate 111 comprises openings 113, through which the very tips of the probes 11 pass. The outer surfaces of the base plate 111 facing the probe heaters 1a and/or facing the sample 120 can be coated with an infrared-reflective coating such as gold, silver, platinum, rhodium, ruthenium, aluminium or platinum.

Furthermore, the internal cavity 103a of the heatsink 103 is shaped so as to provide auxiliary reflectors 115 (see FIG. 3) partially surrounding the probes 11 around approximately ⅔ of their circumference, on the sides opposite to the probe heaters 1a. Thus, the infrared bath effect is maximised, and the heating of the probes 11 is as uniform as possible. Since the very tips of the probes 11 are situated on the opposite side of the base plate 111 to the probe heaters 1a, they are heated by conduction over the small distance to the tips, an area of the distal end of the probes 11 proximate to the base plate 111 being heated.

Finally, as can be best seen on FIG. 3, at least one connecting pad 109 is provided so as to permit electrical connection with thermocouples situated in the probes 11, and is connected to a further electronic device via electrical connections 110. Other thermocouples (not illustrated) may be provided in base plate 111, and/or heatsink 103 at convenient locations so as to measure temperatures and heat fluxes useful for controlling the temperature of the arrangement.

As can be seen on FIG. 2, the heating arrangement further comprises a sample heating module 1b, situated in the materials testing device 100 underneath the base plate 111. This sample heating module 1b is illustrated in more detail in FIG. 4, which shows the module schematically in exploded view. It should be noted that, although the sample heating module 1b described below is particularly advantageous and works particularly well with the probe heater 1b as described above, the combination of the two is not essential. In essence, the probe heater 1b of the invention can be used with any form of sample heater, such as a simple conventional resistive heater.

Figure 4:
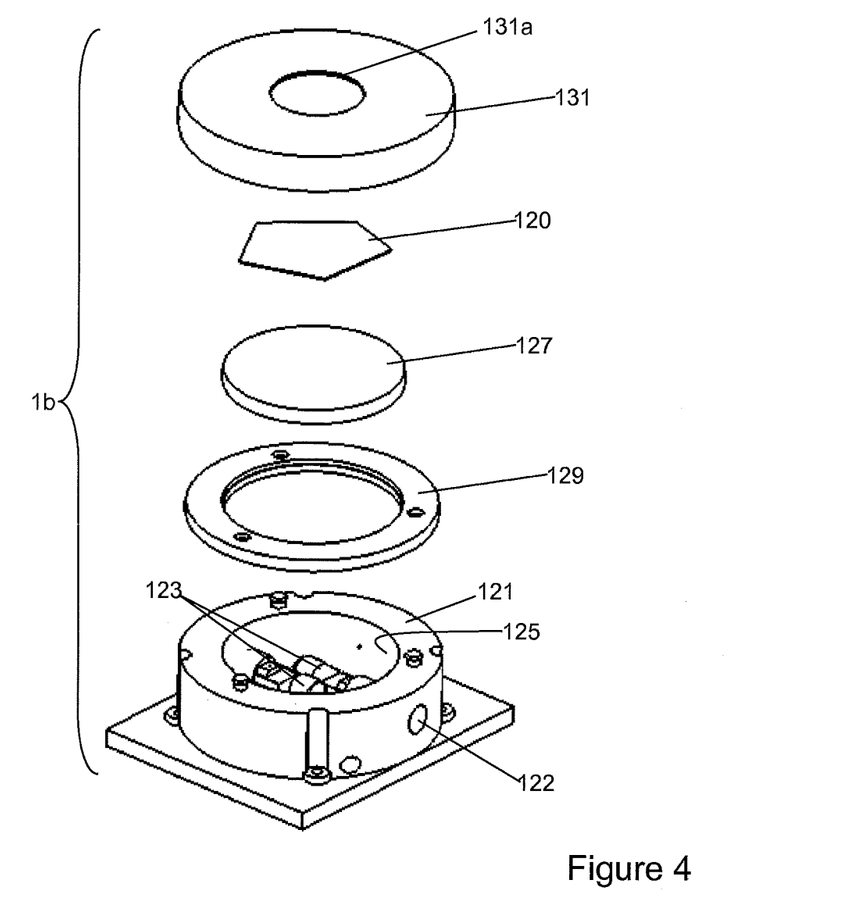
FIG. 4: an exploded view of a sample heater.

Globally, sample heating module 1b serves to position a sample 120 in contact with the tips of the probes 11, and to heat it to the same temperature as the probes 11. Sample heating module 1b will generally be placed on a movable base that can be moved at least in a Z-axial direction, i.e. parallel to the axis of the probes 11. Normally, such a movable base can be moved along all 3 axes of translation X, Y and Z. Alternatively, the sample heating module 1b can be fixed, and the toolhead 101 and all the attached components, or just the probes 11, can be moved instead.

Sample heating module 1b comprises a further reflector 121, inside the concave cavity of which is situated one or more further infrared emitting elements 123, in the present instance halogen lamps, however ceramic heaters, simple coils or similar could equally be used. In the illustrated example, further reflector 121 is of parabolic form and is machined directly into a block of metal such as aluminium, which is watercooled via conduit 122. The further reflecting surface 125 of the further reflector 121 may be coated with a heat reflecting material such as gold, silver, platinum, rhodium, ruthenium, aluminium or platinum. Alternatively, further reflector 121 may be formed as a gold, silver, platinum, rhodium, ruthenium, aluminium or platinum layer on an insulating material such as a ceramic. It is also conceivable that a non-parabolic shape such as a spherical reflector could be provided however the primary advantage of a parabolic reflector is that the distribution of the infrared radiation is as homogeneous as possible.

A sample holder 127 is mounted to the open end of the further reflector 121 via an insulating ring 129, for instance made of a material such as Macor (a machinable glass-ceramic comprising fluorphlogopite mica in a borosilicate glass matrix, as commercialised by Corning), in which the sample holder is bonded, welded, or force-fitted. Other suitable materials comprise heat resistant glasses, ceramics, and glass-ceramics. A particularly suitable material for the sample holder 127 is alumina, since it is opaque in the mid- and far infrared, and thus will absorb a good proportion of the infrared radiation thereby heating the sample holder 127. This heat is then transmitted to the sample 120 predominantly by conduction. Since the reflector 121 is parabolic, the infrared radiation will be travelling in an essentially parallel beam, and thus will impinge on the sample holder 127 as homogeneously possible, heating it as evenly as possible.

To prevent any extraneous infrared radiation which is passed through holes 113 in the base plate 111 from affecting the temperature of the sample 120, and to prevent infrared radiation from the sample heating module 1b from interacting with the tips of the probes 11 as far as possible, an annular cap 131 is provided which covers the insulating ring 129 and part of the sample holder, leaving an opening 131a sufficiently large such that the tips of the probes 11 can pass therethrough to contact a sample 120. The annular cap 131 also extends over the lateral faces of the insulating ring 129 and a part of the further reflector 127 so as to protect the insulating ring 129 from any extraneous infrared radiation. Annular cap 131 is ideally coated both inside and out with an infrared-reflective layer such as gold, silver, platinum, rhodium, ruthenium, aluminium or platinum layer.

In consequence of the proposed heating arrangement, the tips of the probes 11 can be heated to the same temperature as the sample 120, and the materials testing device can be used as is generally known and thus need not be described further.

Although the invention has been described in reference to particular embodiments, these are not to be construed as limiting the scope of the invention, which includes all embodiments falling within the scope of the appended claims.

The invention claimed is:

1. Heating arrangement for a materials testing device, the materials testing device comprising at least one surface measurement probe adapted to be brought into contact with a surface of a sample, the heating arrangement comprising a probe heater and a sample heating module adapted to support the sample;

the probe heater comprising:
an infrared emitting element adapted to emit infrared radiation;
a reflector having a reflective surface arranged to direct said infrared radiation towards a distal end of said surface measurement probe;
wherein the reflector comprises a first focal point and a second focal point, the infrared emitting element being situated substantially at said first focal point; and
the sample heating module comprising:
at least one further infrared emitting element adapted to emit infrared radiation,
a further reflector having a further reflecting surface adapted to direct said infrared radiation emitted by the further infrared emitting element towards the sample;
a sample holder adapted to support said sample, the sample holder being mounted in an insulating ring and situated facing an open face of said further reflector; and
an annular cap covering said insulating ring and a peripheral part of said sample holder.

2. Heating arrangement according to claim 1, wherein the reflector is formed and positioned such that said second focal point is situated substantially at a part of the surface measurement probe.

3. Heating arrangement according claim 1, wherein said reflector is substantially ellipsoidal on at least part of its reflective surface.

4. Heating arrangement according to claim 1, wherein said reflector further comprises a mask section at an open end thereof.

5. Heating arrangement according to claim 1, wherein said infrared emitting element is an incandescent lamp such as a halogen lamp.

6. Heating arrangement according to claim 1, wherein said infrared emitting element is a ceramic heater.

7. Heating arrangement according to claim 1, wherein said reflector comprises an infrared-reflective coating such as a gold, silver, platinum, rhodium, ruthenium, aluminium or platinum coating.

8. Heating arrangement according to claim 1, wherein the further reflecting surface of the further reflector is substantially parabolic.

9. Heating arrangement according to claim 1, wherein said further reflector is comprised in a block provided with a cooling arrangement.

10. Heating arrangement according to claim 9, wherein said further reflecting surface is formed directly on said block.

11. Heating arrangement according to claim 10, wherein said further reflector comprises an infrared-reflective coating such as a gold, silver, platinum, rhodium, ruthenium, aluminium or platinum coating.

12. Heating arrangement according to claim 1, wherein the annular cap is provided with an infrared-reflective coating such as a gold, silver, platinum, rhodium, ruthenium, aluminium or platinum coating on at least one surface thereof.

13. Materials testing device comprising at least one surface measurement probe and a heating arrangement according to claim 1.

14. Materials testing device according claim 13 comprising a headstock adapted to support said surface measurement probe and a heatsink attached to said headstock, the heatsink defining an interior cavity surrounding said surface measurement probe, the probe heater being mounted in a passage provided in the heatsink which opens into said interior cavity.

15. Materials testing device according to claim 14, wherein said reflector is integrally formed in said heatsink.

16. Materials testing device according to claim 14, wherein said interior cavity is provided with an infrared-reflective coating.

17. Materials testing device according to claim 16, wherein said infrared-reflective coating comprises a metal selected from the group consisting of gold, silver, platinum, rhodium, ruthenium, aluminium, and platinum.

* * * * *